United States Patent [19] [11] 4,211,224
Kubach et al. [45] Jul. 8, 1980

[54] FILTER VENTING DEVICES FOR OSTOMY APPLIANCES

[76] Inventors: John S. Kubach, 1406 Milan Rd.; Richard D. Stanley, 164 W. Sprucewood, both of Sandusky, Ohio 44870

[21] Appl. No.: 47,724

[22] Filed: Jun. 12, 1979

[51] Int. Cl.³ .............................................. A61F 5/44
[52] U.S. Cl. ................................................... 128/283
[58] Field of Search .............................. 128/275–276, 128/283, DIG. 24, 294–295

[56] References Cited

U.S. PATENT DOCUMENTS

| 2,054,535 | 9/1936 | Diack | 128/283 |
|---|---|---|---|
| 2,555,086 | 5/1951 | Guinn | 128/283 |
| 2,688,327 | 9/1954 | Berg | 128/283 |
| 3,055,368 | 9/1962 | Baxter | 128/283 |
| 3,478,743 | 11/1969 | Ericson | 128/275 |
| 3,690,320 | 9/1972 | Riely | 128/283 |
| 3,908,656 | 9/1975 | Binard | 128/283 |
| 3,952,727 | 4/1976 | Nolan | 128/283 |

FOREIGN PATENT DOCUMENTS

| 2620129 | 11/1976 | Fed. Rep. of Germany | 128/283 |
|---|---|---|---|
| 1363644 | 8/1974 | United Kingdom | 128/283 |
| 1416594 | 12/1975 | United Kingdom | 128/283 |

Primary Examiner—C. Fred Rosenbaum
Attorney, Agent, or Firm—Paul J. Richardson

[57] ABSTRACT

Waste gases, flatus, are released to the atmosphere through venting devices, attached to post-surgical ostomy appliances, after offensive odors are removed by deodorants impregnated on fibrous or porous granular filters. In the preferred embodiment the venting device is a section of plastic tubing packed with a fibrous filtering material that has been impregnated by a molecular altering deodorant. The deodorized gas is released automatically and continuously at a rate at which there is no buildup of pressure within the appliance or within the patient's body. In pouch-type appliances, the deodorant also effectively removes offensive odors from accumulated liquid and solid waste products. These inexpensive venting devices may be attached to the ostomy appliance during the manufacturing process or they may be purchased separately for use with standard commercially available ostomy appliances.

26 Claims, 31 Drawing Figures

FILTER VENTING DEVICES FOR OSTOMY APPLIANCES

BACKGROUND OF THE INVENTION

In certain surgical operations, such as colostomy, ileostomy, cecostomy, urostomy, ureterostomy type operations, a portion of an abdominal organ is removed altering the normal waste elimination process. Often a segment of the affected organ is diverted so that it protrudes through an incision in the abdominal wall. This protrusion, the stoma, serves as a discharge point for the waste products from the body of the patient who has undergone the surgery.

These patients, hereinafter referred to as ostomates, are unable to exercise control over the elimination of gaseous, liquid or solid body wastes. A variety of post-surgical appliances have been developed to collect and/or prevent the release of these waste products at inopportune times.

These appliances fall into two general classes: ostomy caps and ostomy pouches.

A few ostomates are able to have some control over the elimination functions by using diet control and irrigation techniques. It is sufficient to prevent accidental discharges by placing a cap over the stoma between irrigations. This ostomy cap, or stoma cap, looks like a large band-aid, is constructed of an absorbant material, and is adhesively attached to the abdomen. Said stoma cap absorbs mucous seepage, prevents the discharge of flatus, the gaseous component of the body waste, and prevents the accidental discharge of solid and liquid wastes.

Most ostomates are unable to use the irrigation procedure. They need a reservoir to collect the waste products as they are discharged from the stoma. An impermeable ostomy pouch is fitted around the stoma to prevent the escape of the solid, liquid and gaseous waste products along with the associated foul odors.

There are a number of ostomy pouches, disposable or reusable, commercially available that enable the ostomate to live a more or less normal existance, however, there are problems that have not been satisfactorily resolved that cause the ostomate inconvenience, discomfort, and acute personal embarrassment.

In order to prevent the seepage of liquid and solid wastes from said pouch soiling the ostomate's clothing and person and causing skin disorders; and in order to prevent the embarrassment caused by the escape of the malodorous flatus; it is necessary to have an air-tight containment between the abdomen and said pouch. This air-tight containment is a cause of the first problem: buildup of gas pressure inside the ostomy appliance and inside the abdomen.

The pouch, composed of an impermeable plastic material, initially lies flat against the body but as the gas pressure increases the bag is distended producing a noticeable bulge that is apparent to others unless the ostomate limits himself to wearing loose-fitting and perhaps unfashionable clothing. An increase in gas pressure can also cause acute discomfort and pain to the ostomate; and, the pressure can also become high enough to break the adhesive seal binding the ostomy appliance to the abdomen, releasing a foul odor and the accumulated solid and liquid wastes thus staining the ostomate's clothing and causing acute embarrassment and possible skin irritations.

An additional cause of social embarrassment occurs when the ostomy pouch is emptied and, if, reusable, rinsed out. This may be done in a public rest room but an extremely foul and pervasive odor accompanies the process. The odor eminating from fecal material in an ostomy bag is much more offensive than that associated with normal elimination because the ostomate's digestive tract has been forshortened or altered by the surgery. As a result there is less absorption of the enzymes that act on the waste products producing odorous compounds and less absorption of liquid wastes. In said pouch, in addition to the enzymic activity there is bacterial action that also produces a fetid odor. These reactions are intensified by body heat. While the odor of urine is less strong, essentially the same processes occur to embarrass ostomates who have undergone urostomy or ureterostomy surgery of the bladder, kidney, or uterus. These patients do not however, have a problem with gas pressure and pouch distension.

PRIOR ART

The problem of odorless flatus release has long been recognized. Prior inventions have focused on methods of release and/or deodorization.

Guinn, U.S. Pat. No. 2,555,086, describes a stoma cap containing a filtering material and a perforated screw on cap. Diack's invention, U.S. Pat. No. 2,054,535, is valve actuated with a removable cartridge and requires manual manipulation by the ostomate. This is not easy to do when fully clothed. Riely, U.S. Pat. No. 3,690,320, has a pouch containing a packet of deodorant and a gas permeable membrane to allow a release of flatus. There is no filtering system. Berg, U.S. Pat. No. 2,688,327, describes a girdle that permits flatus release through a charcoal pad. In Baxter, U.S. Pat. No. 3,055,368, flatus is released after passing through horizontal and vertical passages. There is no deodorizing system. In the Nolan invention, U.S. Pat. No. 3,952,727, a patch of woven fiber, impregnated with activated charcoal, is attached to the interior of a pouch. A small slit in said pouch exterior to said patch controls the flatus release rate. In order to deodorize the flatus the rate of release is too slow to avoid distension of said pouch.

The above cited inventions are commendable examples of many efforts to solve the long recognized problems of the unfortunate ostomate. Regrettably they have been only partially effective, and some, Diack for example, require manual operation by the ostomate. This must be done in private and is not possible for an incapacitated ostomate. In addition, all of the cited inventions, except perhaps Nolan, discussed above, would be rather expensive to manufacture and this can be quite important to the ostomate. For collateral reasons: skin sensitivity, penetration of odors into the appliance; reusable pouch should be discarded after five to seven day's use, and disposable appliances are discarded more frequently. The venting devices described in this specification can be very cheaply manufactured.

These devices have been tested and the program is continuing. The plastic tube venting device and the porous granular venting device described in Exemplifications (1) and (2) of the following Summary of the Invention have been successively tested on a number of ostomates, as have variations of said devices. Flatus is released without any detectable odor and with no increase in pressure within the pouch. The pouch, in fact, lies flat against the body. When accumulated solid and liquid wastes are disposed on the odor is effectively reduced to tolerable levels.

SUMMARY OF THE INVENTION

It is an object of this invention to provide improved ostomy appliance venting devices that automatically and continuously release odorless flatus into the atmosphere.

It is further object of this invention to provide improved ostomy appliance venting devices that avoid the accumulation of excess flatus that would cause an increase in pressure in the intestinal tract and be a source of discomfort and potential harm to the ostomate.

It is a further object of this invention to provide improved ostomy venting devices that prevent pouch distension permitting the ostomate to wear fashionable clothing in comfort and with confidence that he will not be embarrassed by an unsightly bulge forming under such clothing.

It is further object of this invention to provide improved ostomy appliance venting devices that automatically, continuously and effectively deodorize the flatus permitting the ostomate to engage in social activities with confidence that he will not be inadvertently embarrassed.

It is a further object of this invention to provide improved ostomy appliance venting devices that reduce to a tolerable level the fetid odor of the liquid and solid fecal matter accumulating in said ostomy appliances so that these waste products may be disposed of in a maner inoffensive to others and unembarrassing to the ostomate.

It is a further object of this invention to provide improved ostomy appliance venting devices that effectively deodorize the liquid waste accumulated in urostomy and ureterostomy pouches.

It is a further object of this invention to provide improved ostomy appliance venting devices that are compatible with any commercially available ostomy appliance, inexpensive to manufacture and to purchase, and that extend the useful life of said appliance.

It is a further object of the invention to provide improved ostomy appliance venting devices that may be inserted in said appliance during the manufacturing process or may be separately purchased and inserted in said appliance.

In all but the fifth exemplification described below, the venting device is positioned so that one end, the exit orifice, is open to the atmosphere and the other end, the entrance orifice, is open to the interior of the ostomy appliance to which said venting device is attached.

Said venting device may be hermetically sealed to said ostomy appliance during the manufacturing process or, in the alternative, said venting device may be purchased separately and inserted in a commercially available ostomy appliance. In the latter case, a slit, or a size that will just permit insertion of said venting device partly into the interior of said ostomy device, it cut in said ostomy appliance at the desired location and said device is positioned in said slit so as to fulfill the orientation conditions of the preceding paragraph. A flange, hermetically sealed to and circumscribing said venting device, has an adhesive coating on one side that produces an air-tight seal between said venting device and said ostomy appliance.

EXEMPLIFICATIONS OF VENTING DEVICES (1) A section of thin-walled flexible plastic tubing is packed with a fibrous filtering material, i.e. porous non-toxic plastic woven fibers, is coated with an effective volatile deodorizing agent. This embodiment of the invention is most frequently inserted in an ostomy pouch but it is adaptable to any type of ostomy appliance. Flatus from the stoma diffuses through said filtering material and escapes, deodorized into the atmosphere. There is no buildup of gas pressure in said pouch and no distension of said pouch. Some of said deodorizing agent evaporates and diffuses into the interior of said pouch reacting with odor producing compounds in the liquid and solid fecal materials that have accumulated in said pouch and, by altering the molecular structure of the compounds, reduces the odor to an inoffensive level.

(2) A cylindrical segment of porous granular filtering material, i.e., an aggregate of small glass beads bonded together to form a porous matrix, is bonded to a circumscribing segment of plastic tubing. Said filter is impregnated with an effective deodorant. This filter venting device may be used with either a stoma cap or an ostomy pouch. When inserted in an ostomy pouch it is positioned above the stoma on the side of said pouch that is away from the body. Release of odorless flatus with no increase in pressure occurs in both types of ostomy appliances. When used in said pouch deodorization of accumulated fecal material occurs in the same manner as in the first exemplification.

(3) The two exemplifications described above may be combined so that both the fibrous filtering material and the porous granular filter are used together. See Detailed Description of FIG. 4, FIG. 27, and FIG. 28 below.

(4) The fibrous material used in Exemplification (1) may also be used with a stoma cap by sealing said fibrous material inside a container constructed of fabric that is inserted in the exterior face of said cap and sealed by one of the two techniques mentioned above.

(5) In an ostomy pouch that collects only urine there is no flatus problem thus no need to vent to the atmosphere. Adaptations of the first three exemplifications may be used to counteract the odor of the urine. If prepared during the manufacturing process the entire device is attached to the interior of said pouch, if said device is separately obtained, the exterior orifice should be sealed with a gas impermeable covering.

In the unlikely event that there is a backflushing problem; i.e., penetration of solid and/or liquid waste into the filtration medium: a gas permeable, liquid impermeable membrane may be bonded to the interior orifice of any of the above venting devices.

DETAILED DESCRIPTION OF THE PREFERRED EMBODIMENTS

Figure 1:
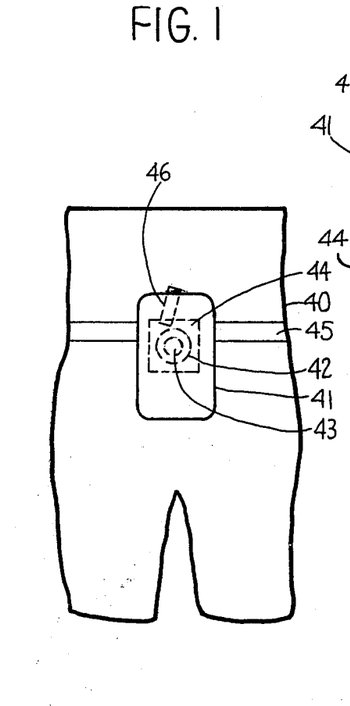
FIG. 1 is a fragmentary view of the abdominal section of a human torso with an ostomy pouch with attached venting device positioned for use.

Referring now to the drawings in more detail, FIG. 1 illustrates a portion of a human torso, 40, with an ostomy pouch, 41, having a stoma sealing gasket, 42, encircling the stoma, 43, and a conventional means, 44, for safely and adhesively securing said pouch to the abdomen to prevent leakage of waste materials. Additional support is sometimes obtained by using a belt, 45. A tubular shaped venting device, 46, the preferred embodiment of the invention, is sealed in the top seam of said pouch, 41. The ostomy appliance shown is in the form of a pouch but the scope of the invention's function is not thereby limited and it is herein understood to represent any type of post-surgical ostomy appliance.

Figure 2:
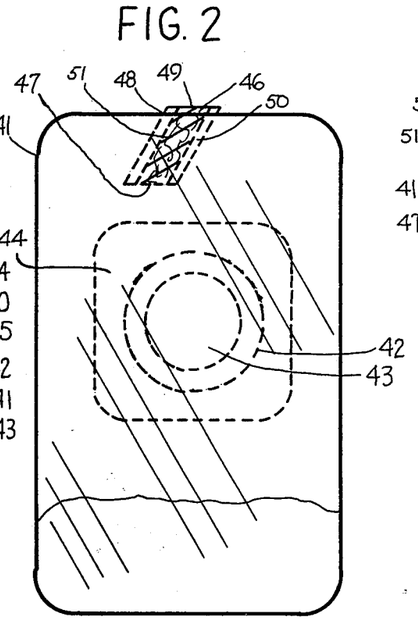
FIG. 2 is an enlarged front elevational view of the ostomy pouch shown in FIG. 1 with a venting device hermetically sealed in said pouch during the manufacturing process.

FIG. 2 is an enlarged elevational view of an ostomy pouch, 41, with said venting device, 46, positioned at an angle from the vertical in order to keep the entrance orifice 47, of said venting device, 46, away from the above and stoma, 42, in order to reduce the possibility of back flushing. As depicted, said venting device, 46, is hermetically sealed during manufacture in the upper seam, 48, of said pouch, 41, so that an exit orifice, 49, is open to the atmosphere and said entrance orifice, 47, is open to the interior of said pouch providing a passage for flatus release. The invention is depicted as a tubular venting device, 46, exemplification (1) in the Summary of the Invention and the Preferred Embodiment. In this embodiment, a section of thin walled, 50, flexible plastic tubing, Tygon or equivalent, satisfying FDA sanitary requirements, serves as the housing of said venting device and has the dimensions: wall thickness—1/32" (0.08 cm.), O.D.—5/16" (0.79 cm), I.D.—¼" 0.63 cm.), and length—1"—(2.54 cm.). The interior of said venting device, 46, is packed with a fibrous filtering material, 51, well known in the art, that is impregnated with a volatile deodorizing agent that alters the molecular structure of odor producing compounds, also well known in the art. Said deodorizing agent reacts with the flatus as it diffuses through said filtering agent, 51, packed in said venting device and some of said deodorizing agent evaporates into the interior of said pouch and reacts with accumulated solid and liquid fecal matter.

Figure 3:
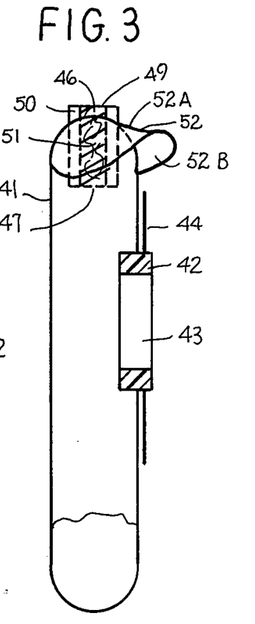
FIG. 3 is an enlarged side elevational view of the ostomy pouch shown in FIG. 1 with a separately insertable venting device inserted into a commercially available ostomy pouch.

FIG. 3 is an enlarged side elevational view of the same pouch, 41, and venting device, 46, depicted in FIGS. 1 and 2. In this Figure, the method of installing said venting device in a commercially available pouch is shown. A 2" (5.08 cm.) diameter annular plastic gas impermeable flange, 52, had been hermetically sealed to the exterior of said venting device at a point ⅛" (0.32 cm.) from the exterior orifice, 49, of said venting device. The upper surface, 52a, of said flange, 52, is untreated but the lower surface, 52b, had been coated with a commercially available adhesive capable of producing an air-tight seal. The coated side of said flange, 52b, had been covered by a removable impervious plastic backing to prevent the adhesion of said flange, 52, under unwanted circumstances prior to use. Said backing is not shown. A slit is cut in said pouch, 41, that is large enough to insert said venting device, 46. The impervious plastic backing is removed from said flange, 52, and said venting device, 46, is inserted into said pouch, 41, through said slit. The underside of said flange, 52b, is then pressed on to the outer surface of said pouch, 41, forming an air-tight seal between said pouch, 41, and said flange, 52. In the FIG. 3, for illustrative purposes, said flange, 52, is shown with the right portion not yet sealed to said pouch.

Figure 4:
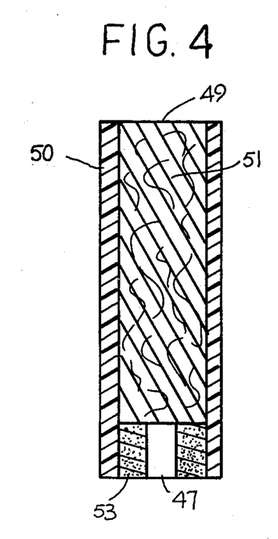
FIG. 4 and FIG. 5 are enlarged front elevational views of alternative venting devices employing the principles of the invention.
Figure 5:
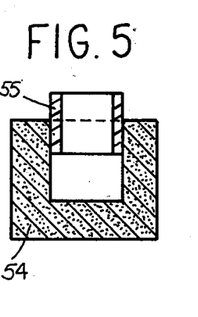

FIG. 4 and FIG. 5 are enlarged front elevational views of modifications of the venting device.

In FIG. 4, the upper part of the device is identical to the device described above, said fibrous filtering material, 51, is impregnated with said deodorizing agent and packed inside a thinwalled flexible plastic tube, 50, of the same dimensions recited in FIG. 2. An annulus of porous granular stone, 53, is bonded inside the interior orifice, 47, of said venting device. The dimensions of said anulus, 53, are: O.D.—¼" (0.63 cm.), I.D.—3/16" (0.48 cm.), and length 1" (2.54 cm.). This is one embodiment of exemplification (3) in the Summary of the Invention. Flatus release and deodorization of flatus, solid and liquid wastes occurs in the manner outlined in FIG. 2. Both of these types of filtering media serve three purposes: (1) to partially block and thus slow down the release of flatus so that deodorization of the flatus can occur prior to its exit from the ostomy appliance, (2) to provide a large surface area that facilitates the molecular alteration of the flatus into inoccuous compounds by a deodorizing agent, and (3) a means of controlling the evaporation of said deodorizing agent into said appliance thus providing a means of deodorizing solid and liquid wastes throughout the life of said appliance. An air-tight seal between said venting device and said ostomy appliance may be formed by either of the methods outlined for the preferred embodiment.

In FIG. 5, a cup-shaped porous, granular filter, 54, having an O.D. of 9/16" (1.43 cm.), an I.D. of 5/16" (0.79 cm.), a length of ⅝" (1.59 cm.), and a cup depth of ⅜" (0.95 cm.), is impregnated with a deodorizing agent. A ¼" (0.63 cm.) section, 55, of the same plastic tubing used in the other venting devices is bonded to the interior of said cup-shaped filter, 54, and positioned in said cup, 54, so that ⅛" (0.32 cm.) protrudes from the top of said cup. This ⅛" protrusion, of said section of plastic tubing, serves as a point of attachment to an ostomy appliance by either of the two methods discussed.

Figure 6:
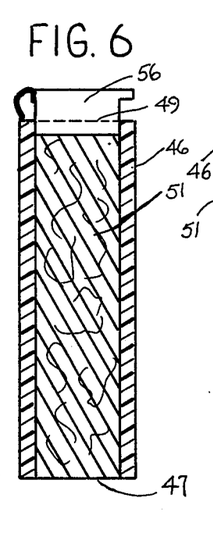
FIG. 6 is an enlarged front elevational view of the embodiment of the invention shown in FIG. 1 and FIG. 2 depicting a selected reclosable closure system and FIG. 7 is an enlarged front elevational view of the invention exhibiting a selected hermetically sealed snip-off-top closure system.
Figure 7:
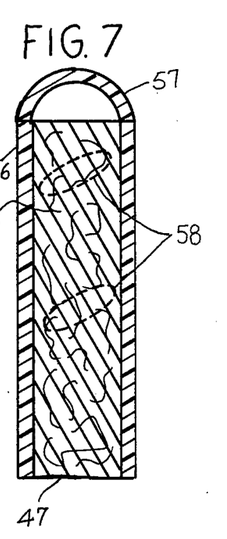
Figure 8:
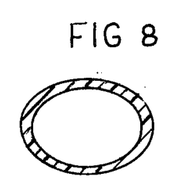
FIGS. 8,9,10,11,12,13,14, and 15 are enlarged cross-sectional views of alternative modifications of the invention.
Figure 9:
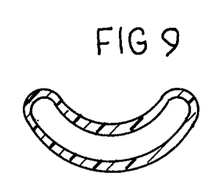
Figure 10:
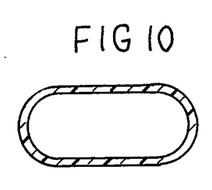
Figure 11:
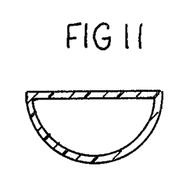
Figure 12:
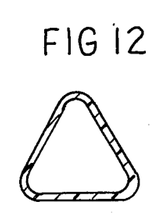
Figure 13:
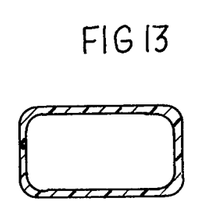
Figure 14:
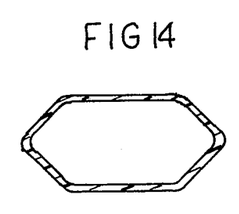
Figure 15:
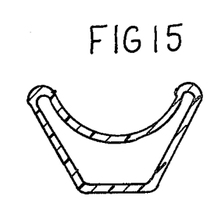
Figure 16:
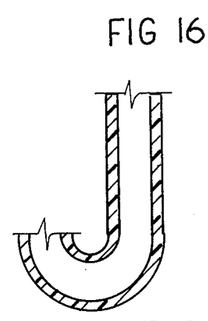
FIGS. 16,17,18,19,20,21,22 and 23 are alternate longitudinal configuration of the invention.
Figure 17:
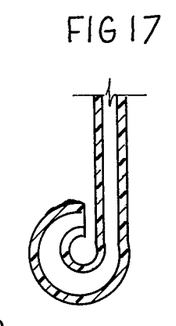
Figure 18:
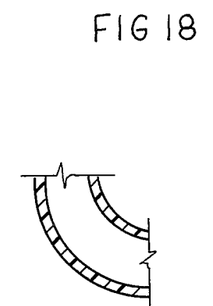
Figure 19:
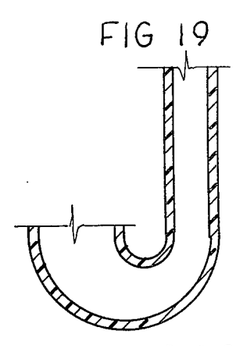
Figure 20:
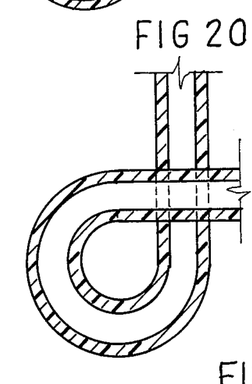
Figure 21:
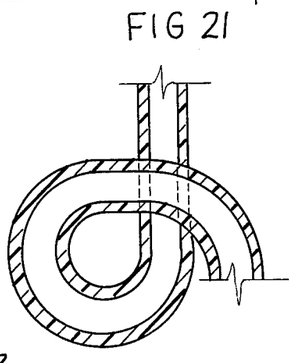
Figure 22:
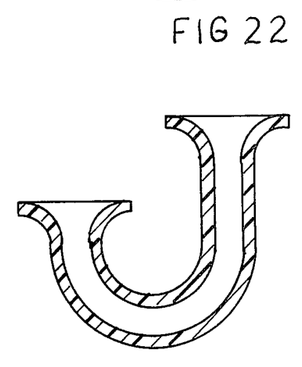
Figure 23:
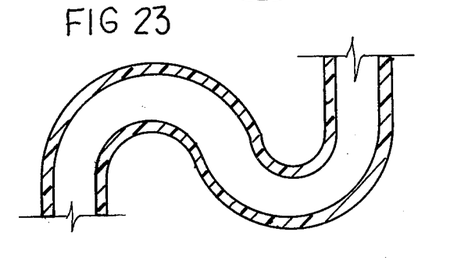

FIG. 6 and FIG. 7 illustrate two closure alternatives that prevent loss of deodorizing action by evaporation or chemical action prior to use.

In FIG. 6 a flanged plastic cap, 56, is partially inserted in the venting device described in FIG. 2, 46. Said cap, 56, is removed prior to use.

In FIG. 7 an extension of said venting device has been hermetically sealed to form a nipple, 57. This nipple, 57, is snipped off with a knife or scissors prior to use.

The closures shown in FIG. 6 and FIG. 7 are adequate when the venting devices are attached to an ostomy pouch during the manufacturing process and the pouch may be folded so as to prevent loss of deodorizing agent from the interior orifice, 47, of said appliance. If purchased separate from the appliance, venting devices should be capped or sealed at both orifices.

Effectiveness of the deodorizing agent may also be preserved by microencapsulation. Said deodorizing agent is sealed in one or more capsules, 58, that have been scored for ease of rupture and stored in the fibrous filtering material. Prior to use, the venting device is squeezed breaking said capsule and releasing said deodorizing agent.

These closure devices are also adaptable to the modification of the venting device shown in FIG. 4.

The deodorizing agent integrety of the modification of the invention shown in FIG. 5 may be preserved by covering the exposed end of said segment of plastic tubing, 55, and if purchased separately, the exposed surface of said cup, 54, with removable adhesive tape.

While not shown, the cross section of the venting devices, thus far described are cylindrical. For comfort, compatibility with appliance, and use under certain articles of clothing, alternate cross sections may be desirable.

FIGS. 8, 9, 10, 11, 12, 13, 14, and 15 are illustrative of some suggested alternate cross sections.

A rare ostomate may have a problem with back-flusing; liquid waste entering the venting device and escaping from the appliance while sleeping or lying down. The preferred embodiment uses a straight or linear piece of plastic tubing.

Configurations designed to minimize the possibility of back-flushing are shown in FIGS. 16, 17, 18, 19, 20, 21, 22, and 23.

Figure 24:
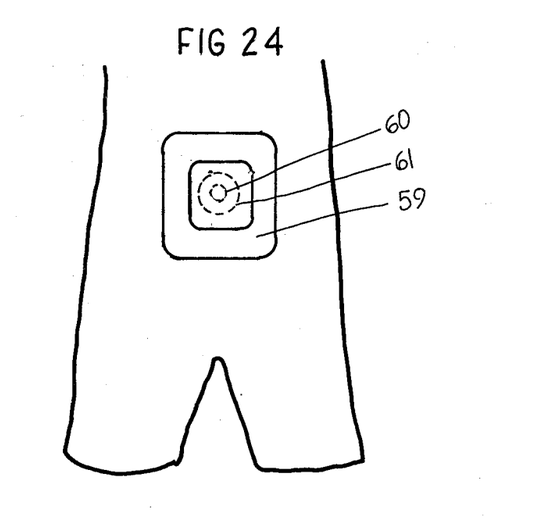
FIG. 24 is a fragmentary view of the abdominal section of a human torso, portraying an ostomy cap or stoma cap embodying the invention and positioned for use.

FIG. 24 illustrates a portion of a human torso with an ostomy appliance attached in the conventional manner. In this illustration said device is a stoma cap, 59, but is understood to represent any type of ostomy appliance, cap or pouch. A venting device, 60, is secured in said stoma cap and centered with respect to the stoma orifice, 61.

Figure 25:
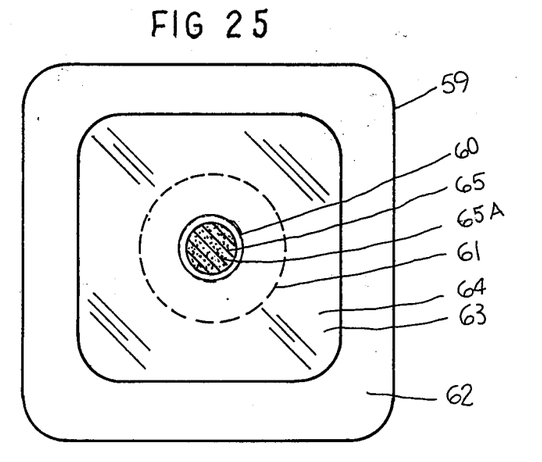
FIG. 25 is an enlarged front elevational view of the ostomy appliance shown in FIG. 24 with a venting device hermetically sealed in said appliance during the manufacturing process.

FIG. 25 is an enlarged front elevational view of said stoma cap, 59, and said venting device, 60. Said stoma cap, 59, is adhesively secured at 62, to the abdomen by conventionally accepted methods. The inner lining, 63, of said stoma cap, 59, is composed of sanitized material designed to absorb any leakage or discharge, while the outer surface, 64, is composed of a plastic impervious material. Near the center of said stoma cap, 59, is positioned a flat wafer or pill-shaped porous granular filter, 65a, permanently bonded to a section of annular plastic, 65, which is inserted and hermetically sealed in said stoma cap, 59, during the manufacturing process. One face or orifice of the pill shaped venting device, 65, is open to the atmosphere and is circumscribed by said impervious plastic material, 64. The other orifice of said venting device, 60, is open to the stoma side of said cap, 59, and protrudes into said sanitized material, 63. Said porous granular filter, 65a, is impregnated with an effective deodorizing agent and serves as a conduit for the release of deodorized flatus to the atmosphere with no build-up of gas pressure.

Figure 26:
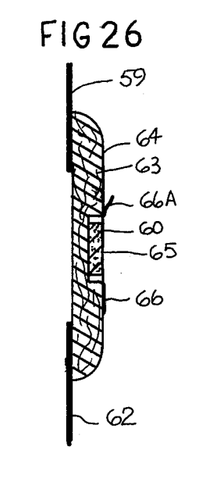
FIG. 26 is an enlarged side elevational view of the ostomy appliance shown in FIG. 24 with a separately insertable venting device inserted into a commercially available ostomy pouch.

FIG. 26 is an enlarged side elevational view of said stoma cap, 59.

Said venting device, 60, has been hermetically sealed to a circumscribing adhesive coated plastic flange, 66, as described in FIG. 3. Said venting device, 60, is inserted in a slit cut in said impervious plastic material, 64, of a commercially available stoma cap, 59. Said coated flange, 66, forms an air-tight seal between said venting device and said impervious plastic material. In FIG. 26 the upper portion of said flange, 66a, is shown not yet sealed to said impervious plastic material.

Said venting device, 60, may also be used with an ostomy pouch, not shown. It may be either hermetically sealed to said pouch, during the manufacturing process at a point above the stoma on the non-stoma side of said pouch or using a flanged venting device as described in FIG. 3 may be inserted through a slit cut in said pouch and attached in the same manner as a tubular venting device is attached in FIG. 3. When used in this manner, there is odorless release of flatus, no build-up of pressure within or distension of said pouch, and accumulated solid and liquid waste odors are reduced to inoffensive levels.

Figure 27:
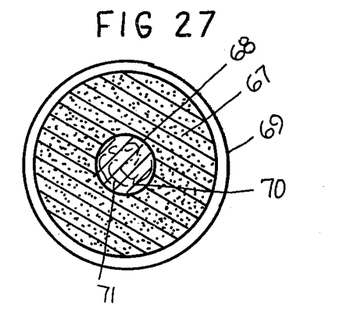
FIG. 27 and FIG. 28 are enlarged front and side elevational views of a modification of a venting device embodying the principles of the invention.
Figure 28:
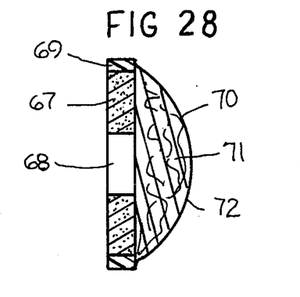

FIG. 27 is an enlarged front elevational view and FIG. 28 is is an enlarged side elevational view of another venting device employing the principles of the invention. This venting device is similar to that in FIG. 4 in that it is another example of exemplification (3) of the Summary of the invention and employs two types of filtering media. An annulus of porous granular material, 67, having a central aperture, 68, is permanently bonded to a circumscribing section of plastic tubing, 69. Said plastic tubing section, 69, is peripherily bonded to a liquid impermeable, gas permeable plastic membrane, 70. The size of said membrane, 70, is such that a cavity is formed between said porous granular filter, 67, and said membrane, 70. Said cavity is packed with fibrous filtering material, 71, that is impregnated with an effective deodorizing agent. Said venting device may be installed in either a stoma cap or ostomy pouch by the alternative procedures previously outlined. When installed the orifice, 72, containing said fibrous material opens to the interior and the other orifice opens to the exterior of said ostomy appliance.

In order to conserve the deodorizing agents in venting devices using porous granular filters, adhesive strips of tape may be used as closures that may be removed prior to use.

Figure 29:
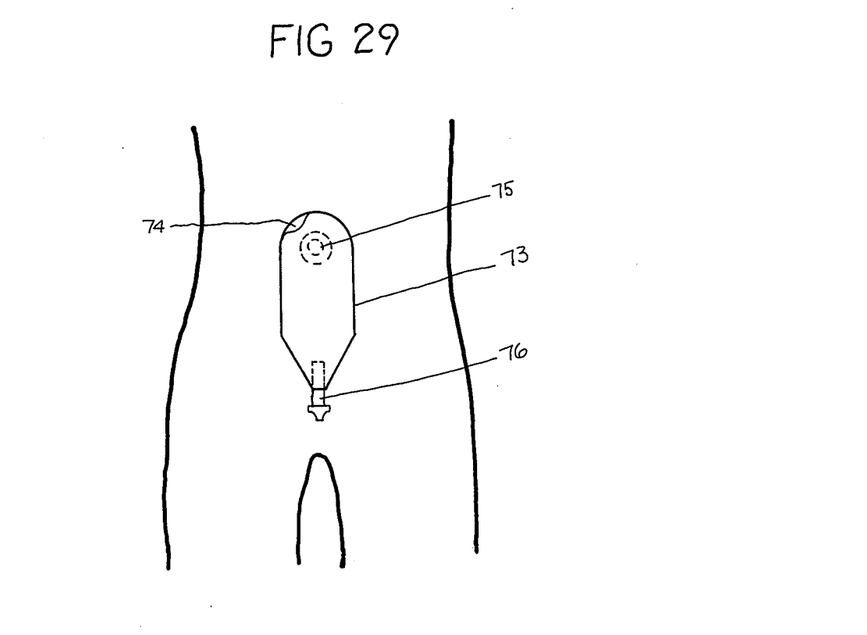
FIG. 29 is a fragmentary view of the abdominal section of a human torso, portraying a urine collecting ostomy appliance embodying the invention and positioned for use.

FIG. 29 illustrates a portion of the human torso with an ostomy appliance secured to the abdomen by a conventionally acceptable system. As illustrated, said appliance is in the form of an airtight ostomy pouch, 73, and will be understood to represent any type of closed system ostomy receptical. This type of appliance may be used where no flatus release occurs. A deodorizing device, 74, is shown positioned above the stoma, 75, and may be any one of the embodiments of the venting devices previously discussed or modifications of said embodiments. If placed in said pouch, 73, during manufacture said deodorizing device, 74, is entirely inside of said pouch, if the alternative method of inserting said device, 74, in a slit cut in a commercially available ostomy pouch, the orifice of said device, 74, that is exterior to said pouch can be sealed with a gas impermeable material. Since the waste product is essentially urine, where this type of appliance is used, said pouch is often equipped with a drainage system, 76.

Figure 30:
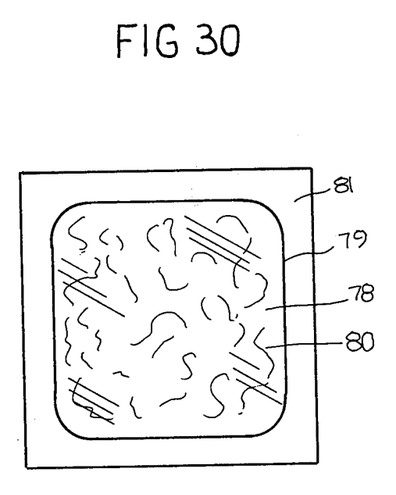
FIG. 30 is an enlarged front elevational view of the venting device depicted in FIG. 29 that is hermetically sealed into the ostomy bag during the manufacturing process.
Figure 31:
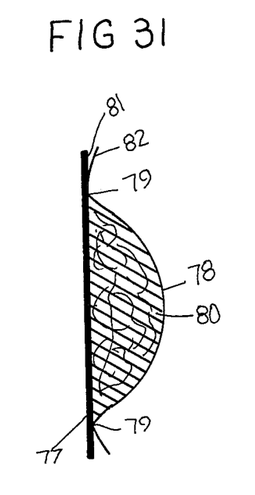
FIG. 31 is an enlarged side elevational view of the venting device depicted in FIG. 29 that is separately inserted in a commercially available ostomy pouch.

FIG. 30 is an enlarged frontal elevation and FIG. 31 is an enlarged side elevation of one embodiment of the invention shown in FIG. 29. The side of said deodorizing device, 74, facing the exterior of said pouch, is constructed of an imprevious plastic material, 77, and is hermetically sealed to the other side of said deodorizing device, which is constructed of a liquid impermeable gas permeable membrane, 78, at the periphery, 79, of said membrane, 78, forming a pocket approximately 1" (6.5 cm.) square. Said pocket is packed with a fibrous filtering material, 80, that has been impregnated with an effective deodorizing agent. Said deodorizing device may be hermetically sealed in the appliance during manufacture, FIG. 30, or said deodorizing device may be separately inserted in a commercially available ostomy appliance, FIG. 31. The exterior impervious plastic material, 77, is coated with an adhesive, capable of maintaining an air-tight seal, on the side, 81, of said imprevious plastic material, 77, that is bonded to said liquid impermeable gas permeable membrane, 78, and in the part of said impervious plastic material, 77, that extends beyond the periphery, 79, of said liquid impermeable gas permeable membrane, 78. A removable rectangular piece of impervious plastic backing, 82, having outer dimensions that are the same as the dimensions of said impervious plastic material, 77, and an aperture with the same dimensions as said periphery, 79, of said liquid permeable gas permeable membrane, 78, is pressed against the adhesive coated side, 81, of said impervious plastic material, 77, preserving the integrety of said adhesive. A slit is cut in the surface of a commercially available closed-system ostomy pouch large enough to insert said liquid impermeable gas permeable membrane, 78, into said pouch, 73. The rectangular piece of impervious plastic backing, 82, is removed from the adhesive coated side of said impervious plastic material, 77, and said liquid impermeable gas permeable membrane, 78, is inserted into said pouch and said impervious plastic material, 77 is pressed against the surface of said pouch, 73, forming an air-tight seal.

During use, odorous wastes that accumulate in said pouch, 73, are deodorized by the deodorizing agent that diffuses through said liquid impermeable gas permeable membrane, 78, into said pouch, 73.

The deodorizing properties of said deodorizing agent may be preserved during storage prior to use by covering said membrane, 78, with strips of removable adhesive tape until ready for use.

For illustrative purposes a liquid impermeable gas permeable membrane, 78, was used to contain the deodorant but the scope of the invention is not thereby limited and any fabric or other material that permits the diffusion of the deodorizing agent into said pouch, 73, is understood to be implied.

In very rare cases there may be a problem of clogging any of the venting devices described by liquid or solid wastes. A gas permeable liquid impermeable membrane may be bonded to the interior orifices of such devices to prevent such clogging.

A number of embodiments of the invention have been disclosed as well as some suggested dimensions. It is to be understood that the scope of the invention is not limited thereby but is susceptible to various modifications and adaptations in different installations as will be apparent to those skilled in the art without departing from the scope of the invention as stated in the following claims.

We claim:

1. A filter venting device for use with post-surgical ostomy appliances providing for the continuous and automatic release of odorless gas, with no increase in gas pressure or distension of said ostomy appliance and providing for the deodorization of gaseous, liquid and solid waste materials deposited and collected in said ostomy appliance, comprising:
    a section of plastic tubing;
    fibrous filtering material, packed inside said section of plastic tubing;
    a molecular altering deodorizing agent impregnating the strands of said fibrous filtering material;
    an air-tight sealing means between said ostomy appliance and the outer surface of said section of plastic tubing, whereby one orifice, the exterior orifice, of said section of plastic tubing is open to the atmosphere and the exterior of said ostomy appliance and the other orifice, the interior orifice, of said section of plastic tubing is open to the interior of said ostomy appliance; and
    a closure means whereby deodorizing properties of said deodorizing agent are preserved until said filter venting device is ready for use.

2. A filter venting device as recited in claim 1, wherein said air-tight sealing means, comprises:
    a plastic circular flange circumscribing the outer surface of said segment of plastic tubing, said flange being hermetically sealed to said outer surface of said plastic tubing;
    an adhesive coating on one side of said flange capable of producing an air-tight seal; and
    an impervious plastic backing covering the coated side of said flange, said plastic backing being removable permitting an air-tight seal when the exposed coated side of said flange is pressed against a region of the surface of a commercially available ostomy appliance surrounding a slit, cut in said ostomy appliance surface, through which the interior orifice of said filter venting device has been inserted.

3. A filter venting device as recited in claim 1, wherein said closure means are removable caps fitting tightly into the ends of said section of plastic tubing.

4. A filter venting device as recited in claim 1, wherein said closure means are hermetically sealed extensions of the ends of said section of plastic tubing that may be cut off prior to use of said filter venting device.

5. A filter venting device as recited in claim 1, wherein said closure means are scored, microencapsulations, easily ruptured capsules, containing said deodorizing agent, and embedded in said fibrous filtering agent.

6. A filter venting device as recited in claim 1, wherein the cross sectional configuration of said filter venting device is circular.

7. A filter venting device as recited in claim 1, wherein the longitudinal configuration of said filter venting device is linear.

8. A filter venting device as recited in claim 1, wherein a gas permeable liquid permeable membrane is peripherally bonded to the interior orifice of said filter venting device.

9. A filter venting device for use with post-surgical ostomy appliances providing for the continuous and automatic release of odorless gas, with no increase of gas pressure or distension of said ostomy appliance and providing for the deodorization of gaseous, liquid and solid waste materials deposited and collected in said ostomy appliance comprising:
 a pill-shaped porous granular filter;
 an annulus of plastic tubing circumscribing and bonded to said porous granular filter;
 a molecular altering deodorizing agent impregnating said porous granular filter;
 an air-tight sealing means between said ostomy appliance and the outer surface of said annulus of plastic tubing whereby one orifice, the exterior orifice, of said filter device is open to the atmosphere and the exterior of said ostomy appliance and the other orifice, the interior orifice, is open to the interior of said ostomy appliance; and
 a closure means whereby deodorizing properties of said deodorizing agent are preserved until said filter venting device is ready for use.

10. A filter venting device as recited in claim 9, wherein said air-tight sealing means, comprises:
 a plastic circular flange circumscribing the outer surface of said segment of plastic tubing, said flange being hermetically sealed to said outer surface of said plastic tubing;
 an adhesive coating on one side of said flange capable of producing an air-tight seal; and
 an impervious plastic backing covering the coated side of said flange, said plastic backing being removable permitting an air-tight seal when the exposed coated side of said flange is pressed against a region of the surface of a commercially available ostomy appliance surrounding a slit, cut in said ostomy appliance surface, through which the interior orifice of said filter venting device has been inserted.

11. A filter venting device as recited in claim 9, wherein said closure means are strips of adhesive tape sealing said orifices of said filter venting device.

12. A filter venting means as recited in claim 9, wherein a gas permeable liquid impermeable membrane is peripherally bonded to said interior orifice of said filter venting device.

13. A filter venting device for use with post-surgical ostomy appliances providing for the continuous and automatic release of odorless gas, with no increase of pressure or distension of said ostomy appliance and providing for the deodorization of gaseous, liquid and solid waste materials deposited and collected in said ostomy appliance, comprising:
 a section of plastic tubing;
 fibrous filtering material, packed inside one part of said section of plastic tubing;
 a molecular altering deodorizing agent impregnating the strands of said fibrous filtering material;
 an annulus of pourous granular filter, bonded to the inside of the remaining part of said section of plastic tubing not packed with said fibrous filtering material;
 an air-tight sealing means between said ostomy appliance and the outer surface of said section of plastic tubing, whereby one orifice of said section of plastic tubing is open to the atmosphere and the exterior of said ostomy appliance and the other orifice of said section of plastic tubing is open to the interior of said ostomy appliance; and
 a closure means whereby deodorizing properties of said deodorizing agent are preserved until said filter venting device is ready for use.

14. A filter venting device as recited in claim 13, wherein said air-tight sealing means, comprises:
 a plastic circular flange circumscribing the outer surface of said segment of plastic tubing, said flange being hermetically sealed to said outer surface of said plastic tubing;
 an adhesive coating on one side of said flange capable of producing an air-tight seal; and
 an impervious plastic backing covering the coated side of said flange, said plastic backing being removable permitting an air-tight seal when the exposed coated side of said flange is pressed against a region of the surface of a commercially available ostomy appliance surrounding a slit, cut in said ostomy appliance surface, through which the interior orifice of said filter venting device has been inserted.

15. A filter venting device as recited in claim 13, wherein said closure means are removable caps fitting tightly into the ends of said section of plastic tubing.

16. A filter venting device as recited in claim 13, wherein said closure means are hermetically sealed extensions of the ends of said section of plastic tubing that may be cut off prior to use of said filter venting device.

17. A filter venting device as recited in claim 13, wherein said closure means are scored, microencapsulations, easily ruptured capsules, containing said deodorizing agent, and embedded in said fibrous filtering agent.

18. A filter venting device for use with post-surgical ostomy appliances providing for the continuous and automatic release of odorless gas, with no increase in gas pressure or distension of said ostomy appliance and providing for the deodorization of gaseous, liquid and solid waste materials deposited and collected in said ostomy appliance, comprising:
 a cylindrically shaped porous granular filter one face of said porous granular filter having a centrally positioned cylindrical cavity extending a distance into said filter that is less than the distance to the other face of said porous granular filter, giving said porous granular filter a cup-shaped appearance;
 a section of plastic tubing bonded to the walls of said cylindrical cavity in said porous granular filter and extending beyond and external to the cavity containing face of said porous granular filter;
 a molecular altering deodorizing agent impregnating said porous granular filter;
 an air-tight sealing means between said ostomy appliance and the outer surface of the external part of said segment of plastic tubing, whereby said segment of plastic tubing is open to the atmosphere and the exterior of said ostomy appliance and said porous granular filter is contained in the interior of said ostomy appliance; and a closure means whereby deodorizing properties of said deodorizing agent are preserved until said filter venting device is ready for use.

19. A filter venting device as recited in claim 18, wherein said air-tight sealing means, comprises:
   a plastic circular flange circumscribing the outer surface of said segment of plastic tubing, said flange being hermetically sealed to said outer surface of said plastic tubing;
   an adhesive coating on one side of said flange capable of producing an air-tight seal; and
   an impervious plastic backing covering the coated side of said flange, said plastic backing being removable permitting an air-tight seal when the exposed coated side of said flange is pressed against a region of the surface of a commercially available ostomy appliance surrounding a slit, cut in said ostomy appliance surface, through which said filter has been inserted.

20. A filtering device as recited in claim 18, wherein said closure means are removable strips of adhesive covering the exterior end of said segment of plastic tubing and the exposed surface of said porous granular filter.

21. A filter venting device for use with post-surgical ostomy appliances providing for the continuous and automatic release of odorless gas, with no increase in gas pressure or distension of said ostomy appliance and providing for the deodorization of gaseous, liquid and solid waste materials deposited and collected in said ostomy appliance, comprising:
   a pill-shaped porous granular filter having a centrally located cylindrical aperture extending from one face of said porous granular filter to the other face of said porous granular filter;
   an annular of plastic tubing circumscribing and bonded to said porous granular filter;
   a liquid impermeable gas permeable membrane peripherally bonded to said annulus of plastic tubing and large enough to form a cavity with one face of said porous granular filter;
   fibrous filtering material packed into said cavity formed by said membrane and said porous granular filter;
   a molecular altering deodorizing agent impregnating the strands of said fibrous filtering material;
   an air-tight sealing means between said ostomy appliance and the outer surface of said annulus of plastic tubing whereby said porous granular filter is open to the atmosphere and the exterior of said ostomy appliance and said membrane is contained in the interior of said ostomy appliance; and
   a closure means whereby deodorizing properties of said deodorizing agent are preserved until said filter venting device is ready for use.

22. A filter venting device as recited in claim 21, wherein said air-tight sealing means, comprises:
   a plastic circular flange circumscribing the outer surface of said segment of plastic tubing, said flange being hermetically sealed to said outer surface of said plastic tubing;
   an adhesive coating on one side of said flange capable of producing an air-tight seal; and
   an impervious plastic backing covering the coated side of said flange, said plastic backing being removable permitting an air-tight seal when the exposed coated side of said flange is pressed against a region of the surface of a commercially available ostomy appliance surrounding a slit, cut in said ostomy appliance surface, through which said membrane has been inserted.

23. A filtering device as recited in claim 20, wherein said closure means are strips of removable adhesive tape covering said membrane and the exposed surface of said porous granular filter.

24. A filter venting device for use with post-surgical closed system ostomy appliances providing for the deodorization of waste materials deposited and collected in said ostomy appliance, comprising:
   a sheet of impervious plastic;
   a liquid impermeable gas permeable membrane, peripherally bonded to one side of said sheet of impervious plastic, leaving an exposed border of said sheet of impervious plastic extending beyond the of said liquid impermeable gas permeable membrane, and said membrane forming a cavity between said membrane and said sheet of impervious plastic;
   a fibrous filtering material packed in said cavity formed by said membrane and said sheet of impervious plastic;
   a molecular altering deodorizing agent impregnating the strands of said fibrous filtering material;
   an air-tight sealing means between said closed system ostomy appliance and said sheet of impervious plastic, whereby said sheet of impervious plastic is external to said ostomy appliance and said liquid impermeable gas permeable membrane is sealed in the interior of said ostomy appliance; and
   a closure means whereby deodorizing properties of said filter venting device are preserved until said filter venting device is ready for use.

25. A filter venting device as recited in claim 24, wherein said air-tight sealing means, comprises:
   an adhesive coating on said exposed border of said impervious plastic sheet on the side of said impervious plastic sheet bonded to said liquid impermeable gas permeable membrane; and
   an impervious plastic backing having outer dimensions that are the same as the dimensions of said impervious plastic sheet and an aperture having the same dimension as the periphery of said liquid permeable gas permeable membrane, attached to said exposed border of said impervious plastic sheet, said plastic backing being removable, permitting an air-tight seal when said coated border of said impervious plastic material is pressed against a region of the surface, of a commercially available ostomy appliance, surrounding a slit, cut in said ostomy appliance surface through which said liquid impermeable gas permeable membrane has been inserted.

26. A filter venting device as recited in claim 24, wherein said closure means are strips of removable adhesive tape covering said membrane.

* * * * *